United States Patent
Puchacz et al.

(10) Patent No.: US 10,047,141 B2
(45) Date of Patent: *Aug. 14, 2018

(54) METHOD OF MANUFACTURING A PROTEIN BY PERFUSION IN MEDIA WITH A LOW AMINO ACID CONCENTRATION

(71) Applicant: Coherus Biosciences, Inc., Redwood City, CA (US)

(72) Inventors: Ela Puchacz, Pleasanton, CA (US); James Russell Grove, Mountain View, CA (US)

(73) Assignee: Coherus Biosciences, Inc., Redwood City, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 14/609,225

(22) Filed: Jan. 29, 2015

(65) Prior Publication Data
US 2015/0210750 A1   Jul. 30, 2015

Related U.S. Application Data

(60) Provisional application No. 61/933,665, filed on Jan. 30, 2014.

(51) Int. Cl.
| | | |
|---|---|---|
| *C12N 15/79* | (2006.01) | |
| *C07K 14/715* | (2006.01) | |
| *C12P 21/00* | (2006.01) | |
| *C12N 5/00* | (2006.01) | |
| *C12M 1/00* | (2006.01) | |
| *C07K 14/525* | (2006.01) | |
| *C07K 16/24* | (2006.01) | |
| *C07K 19/00* | (2006.01) | |
| *C12N 5/16* | (2006.01) | |

(52) U.S. Cl.
CPC ......... *C07K 14/7151* (2013.01); *C12M 29/10* (2013.01); *C12N 5/0018* (2013.01); *C12N 15/79* (2013.01); *C12P 21/00* (2013.01); *C12P 21/005* (2013.01); *C07K 14/525* (2013.01); *C07K 14/715* (2013.01); *C07K 16/24* (2013.01); *C07K 19/00* (2013.01); *C07K 2319/30* (2013.01); *C12N 5/16* (2013.01)

(58) Field of Classification Search
None
See application file for complete search history.

(56) References Cited

U.S. PATENT DOCUMENTS

| | | |
|---|---|---|
| 2008/0108106 A1 | 5/2008 | Wang et al. |
| 2009/0068705 A1 | 3/2009 | Drapeau et al. |
| 2011/0091936 A1 | 4/2011 | Gawlitzek et al. |
| 2013/0150554 A1 | 6/2013 | Melville et al. |
| 2013/0224855 A1 | 8/2013 | Gupta et al. |

FOREIGN PATENT DOCUMENTS

| | | | | |
|---|---|---|---|---|
| WO | WO 2004058944 A2 * | 7/2004 | ....... | C07K 14/70521 |
| WO | 2011/134920 A1 | 11/2011 | | |
| WO | WO 2011134920 A1 * | 11/2011 | .......... | C12N 5/0018 |
| WO | 2013/006479 A2 | 1/2013 | | |

OTHER PUBLICATIONS

International Search Report for corresponding PCT Application No. PCT/US2015/013524 dated May 7, 2015.
Heidemann R et al., "The Use of Peptones as Medium Additives for the Production of a Recombinant Therapeutic Protein in High Density Perfusion Cultures of Mamalian Cells", Cytotechnology, Kluwer Academic Publishers, Dordrecht, NL, vol. 32, (Jan. 1, 2000), pp. 157-167, XP000973160.
P. Hossler et al., "Optimal and consistent protein glycosylation in mammalian cell culture", Glycobiology, vol. 19, No. 9, (Jun. 3, 2009), pp. 936-949, XP55112498.
Altamirano et al., "Strategies for fed-batch cultivation of t-PA producing CHO cells: substitution of glucose and glutamine and rational design of culture medium", Journal of Biotechno, Elsevier, Amsterdam, NL, vol. 110, (May 27, 2004), pp. 171-179, XP007914292.
Bonarius Hendrik P J et al., "Metabolic-flux analysis of continuously cultured hybridoma cells using 13CO2 mass spectrometry in combination with 13C-lactate nuclear magnetic resonance spectroscopy and metabolite balancing", Biotechnology and Bioengineering—Combinatorial Chemistry, Wiley, New York, NY, US, vol. 74, No. 6, (Sep. 20, 2001), pp. 528-538, XP002331308.
Reinhart D. et al., Benchmarking of commercially available CHO cell culture media for antibody production. BMC Proceedings, (Dec. 4, 2013), vol. 7, No. Supp 6, p. 13, table 1.

* cited by examiner

*Primary Examiner* — Zachary C Howard
(74) *Attorney, Agent, or Firm* — Rothwell, Figg, Ernst & Manbeck, P.C.

(57) ABSTRACT

Perfusion media are disclosed providing excellent cell density, titer and product quality for production of a therapeutic protein in a perfusion process.

14 Claims, 7 Drawing Sheets

METHOD OF MANUFACTURING A PROTEIN BY PERFUSION IN MEDIA WITH A LOW AMINO ACID CONCENTRATION

FIELD OF INVENTION

The present invention pertains to media suitable for a manufacturing a therapeutic protein in a perfusion process.

BACKGROUND OF THE INVENTION

Proteins such as those intended for pharmaceutical applications can be manufactured using either a batch, fed batch method or a perfusion method. The present invention is directed to perfusion processes, including those used for manufacture of therapeutic proteins.

Perfusion processes for manufacturing therapeutic proteins are sensitive to changes in the composition of culture media, temperature, accumulation of metabolic wastes, and bioreactor physico-chemical parameters. Inadequate or fluctuating conditions affect protein posttranslational modifications such as its glycoprofile, the latter being known to correlate with pharmacokinetic properties.

Perfusion processing is desirable over fed-bath processing because it enables production of more product in a given period of time with improved cost of goods. Hence it is desirable to overcome the challenges of developing suitable feed conditions that will support a perfusion process.

U.S. Pat. No. 7,300,773 and EP 1,781,802 disclose production of the fusion protein TNFR-IG using a fed batch process in which feed media are prescribed having specified concentrations of amino acids and/or inorganic ions.

SUMMARY OF THE INVENTION

Figure 1:
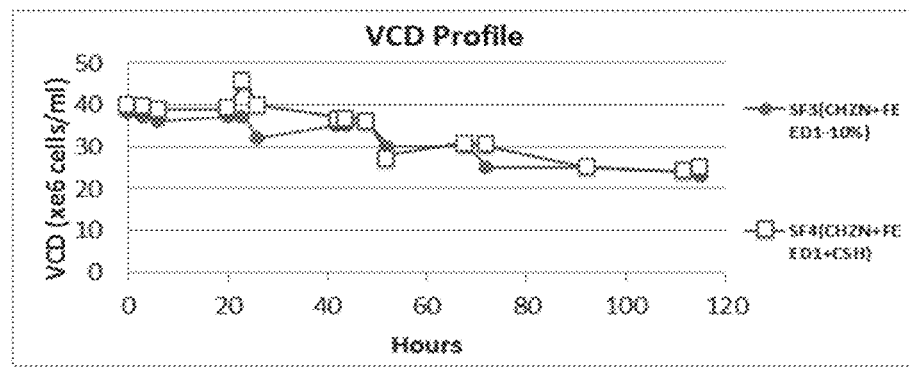
FIG. 1 is a chart of viable cell density (VCD) of cultures containing the lower concentrations feeds (SF3 and SF4) in accordance with the present invention.

We have now discovered that the media used in a perfusion process must be substantially less rich in terms of nutrient content, in particular amino acid content, than media intended for use in a batch or fed batch process. For purposes hereof, nutrient content should be understood as the concentration of given nutrients in the perfusion reactor volume. In particular, our invention concerns a perfusion process in which perfusion is conducted in the presence of a feed medium containing a total amino acid concentration less than or equal to 70 mM and preferably in the range of about 15 mM to about 65 mM. In various embodiments of the invention the total amino acid concentration is in a range selected from: about 15 to 20 mM; about 20 to 25 mM; about 25 to 30 mM; about 30 to 35 mM; about 35 to 40 mM; about 40 to 45 mM; about 45 to 50 mM; about 50 to 55 mM; about 55 to 60 mM; about 60 to 65 mM; and between 65 and 70 mM.

The total amino acid concentrations prescribed herein are less than those recommended for both fed batch and perfusion processes in U.S. Pat. No. 7,300,773. By way of comparison, U.S. Pat. No. 7,300,773 requires a total amino acid concentration above 70 mM. Notwithstanding the assertion in the '773 patent that such concentrations would be understood by persons skilled in the art as capable of being employed in perfusion systems (see column 18, lines 5 to 11), the present disclosure is based in part on our finding, to the contrary, that conducting a perfusion process for manufacture of a therapeutic protein using feed media satisfying the high total amino acid concentrations prescribed in the '773 patent results in production of substantially reduced amounts of the desired protein, and therefore, that the amino acid concentrations in media intended for perfusion must necessarily be reduced, and preferably substantially reduced, in terms of total amino acid concentration. Provided that amino acid concentration constraints of the present invention are met, it should be understood by persons skilled in the art that various non-amino acid components typically employed in feed media (e.g. vitamins, hydrolysates, etc.) may be adjusted empirically in a known manner without departing from the spirit and scope of the present teaching.

In further embodiments of the invention, a perfusion process for manufacturing a biological protein employs feed media satisfying the reduced total amino acid concentration referenced above, and where the feed media is further characterized by one or more of the following criteria: a molar glutamine to cumulative asparagine ratio of greater than 2; a molar glutamine to total amino acid concentration ratio of greater than 0.2; a molar inorganic ion to total amino acid ratio of greater than 1; and a combined amount of glutamine and asparagine per unit volume of less than 16 mM. These criteria should be understood as denoting steady state concentrations and amounts in the perfusion reaction vessel.

Our invention further concerns modifying a feed medium that is otherwise suitable for fed batch production of a therapeutic protein in order to render such medium suitable for use in a perfusion process for manufacturing the protein, where the modification comprises reducing the nutrient richness of the fed batch medium such that, when used in the perfusion reactor, the total amino acid concentration of the feed media is in the range of about 40 to about 95 percent, and preferably about 50 to about 70 percent of the total amino acid concentration of the fed-batch feed medium. Preferably, this method achieves either or both of (i) a production titer comparable to that achievable with a fed batch process using the higher-nutrient feed; and/or (ii) a substantial reduction in the levels of ammonia that would otherwise be generated in the perfusion reactor if such perfusion process were conducted using the same media as that used in a fed batch process.

In an embodiment of the invention, the perfusion method uses the following steps: (a) preparing a mixture comprising cells capable of expressing a desired therapeutic protein, and a culture medium suitable for conducting such expression; (b) in a suitable vessel containing the mixture, causing the cells to produce the protein; and (c) periodically or continuously removing spent culture medium from, and adding fresh culture medium to, the reaction vessel.

The invention can be applied to the manufacture of any therapeutic protein. In an embodiment hereof, the therapeutic protein can be selected from any fusion protein or any antibody. Fusion proteins can include TNFR-Fc (sometimes referred to as TNFR-Ig) fusion proteins. Antibodies can include anti-TNF antibodies. Further non limiting examples of proteins suitable for manufacture in the present invention include etanercept, rituximab, adalimumab, trastuzumab, bevacizumab, eculizumab and natalizumab, as well as biosimilar or bio better variants thereof. It should be understood that the perfusion process of the invention is not limited to any specific therapeutic protein. Thus other proteins than those mentioned here can be produced, such as, e.g, erythropoetins.

In a further embodiment, the invention is a method for producing a therapeutic protein comprising the steps of (a) preparing a mixture comprising CHO cells capable of expressing the protein, and a culture medium suitable for conducting such expression; (b) in a suitable vessel containing the mixture, causing the cells to produce the protein; and (c) periodically or continuously removing spent culture medium from, and adding fresh culture medium to, the reaction vessel, wherein the culture medium comprises (i) a total amino acid concentration of about 15 to about 65 mM; and at least one of: a suitable base media (e.g., SFM4CHO, BalanCD CHO Growth A, HyCell CHO, etc.), a complex chemically-defined feed (e.g., BalanCD CHO Feed 1), dexamethasone, ManNAc, cottonseed hydrolysate and D-(+)-galactose.

In a further embodiment of the perfusion method, prior to step (a), the cells capable of expressing etanercept are grown in a growth phase at a temperature selected from; (i) about 28 to about 37° C.; and (ii) about 35° to about 36° C.

In another embodiment of the perfusion method, during production of the etanercept occurring in steps (b) and (c), above, the reaction vessel is maintained at a temperature selected from (i) greater than about 32° C.; (ii) greater than about 34° C.; (iii) greater than about 35° C.; (iv) the range of about 33° C. to about 36° C.; (v) the range of about 35° C. to about 36° C.; (vi) 32.5° C.; (vii) 33.5° C.; (viii) 34.5 C; and (ix) 35.5° C. The ability to produce excellent product quality, properly folded proteins, and excellent titers at these temperatures is surprising and unexpected given contrary teachings in the art directed to the use of lower temperatures during the production phase (as compared to the growth phase) in a protein manufacturing process.

As a composition of matter, our invention is directed to a media composition formulated to provide a desired total amino acid concentration in a perfusion process for manufacturing a therapeutic protein, wherein the desired concentration, based on the volume of a perfusion reactor used in such process, is in a range selected from the group consisting of about 15 to 20 mM; about 20 to 25 mM; about 25 to 30 mM; about 30 to 35 mM; about 35 to 40 mM; about 40 to 45 mM; about 45 to 50 mM; about 50 to 55 mM; about 55 to 60 mM; about 60 to 65 mM, and wherein the composition when offered, recommended or advertised for sale is accompanied by written or verbal recommendations or instructions supporting or suggesting its intended use in such perfusion process.

A further composition embodiment of the invention is a feed media composition comprising a total amino acid concentration in a range selected from the group consisting of about 15 to 20 mM; about 20 to 25 mM; about 25 to 30 mM; about 30 to 35 mM; about 35 to 40 mM; about 40 to 45 mM; about 45 to 50 mM; about 50 to 55 mM; about 55 to 60 mM; about 60 to 65 mM, and further comprising at least one of, and preferably at least one of the following: cottonseed hydrolysate, dexamethasone, ManNAc, and/or D-(+)-Galactose.

In any of the above embodiments, a preferred range of amino acid concentration is about 15 to about 30 mM and the media can include defined and non-defined media.

Terms such as "culture," "cell density," "cell viability," "titer," "medium" (or "media") "seeding," "growth phase," "production phase," may be understood to have the meanings well understood in the art. For example, reference may be had to U.S. Pat. No. 7,300,773.

DETAILED DESCRIPTION OF THE INVENTION

The present invention provides methods of manufacturing a fusion protein or an antibody via the process known as perfusion. The term "perfusion" as used herein is intended to generally denote a process in which a suspension cell culture is continuously or periodically, and most preferably continuously, supplied with fresh medium to a bioreactor while spent culture media is continuously removed, i.e., harvested (preferably with the product) in order that product contained therein can be continuously harvested, and the waste and toxic materials present in the spent medium can be removed from the bioreactor. Using appropriate filtration means well known in the art, the cells are then continuously filtered from the harvest stream and returned to the bioreactor to maintain a constant culture volume. Such a process, typically carried out continuously, allows the cells to reach high densities. Accordingly, densities as high as 10-75 million cells/mL can routinely be reached and maintained for extended periods of time, e.g. at least two weeks, and typically 20 to 60 days. This can result in very highly productive cell culture process that can produce for a longer period of time as opposed to batch or fed-batch cultures. Alternatively, rather than continuously harvesting product from the removed spent medium, the product can be maintained and concentrated in the culture, and then harvested periodically, or at the end of the culture. As is well known in the art, utilization of appropriately sized filters can allow for removal of only waste, with retention of the recombinant product in the bioreactor culture. An object of the present invention is to provide an appropriate feed media for use in a perfusion process, in particular processes for manufacturing therapeutic proteins such as fusion proteins or antibodies.

Cell culture perfusion processes can typically undergo a feed medium exchange rate of 0.5 to 2 bioreactor volume per day. The present invention is based on our discovery that such perfusion processes will not require as high a concentration of nutrients as that typically employed in feed media used in fed batch processing, and, in fact, will require substantially lesser concentrations. In particular, we have found that the concentration of nutrients, in particular the concentration of amino acids, used in fed batch processes for manufacturing a therapeutic protein (e.g., a fusion protein or antibody) must be reduced to levels that, on the one hand, are still sufficiently nutrient-rich to support the cells' metabolic needs at steady-state levels, but on the other hand not so high in nutrients as to cause other deleterious effects, such as, among other things, the overproduction of ammonia or lactate, which will reduce culture viability, overall titer and product quality. The invention requires reduced nutrients levels in terms of reduced total amino acid concentration levels. Additional nutrient components may be empirically determined in a well-known manner based on cell density, perfusion rate, and specific productivity rate (pcd), provided the resulting reduced nutrient level falls within the overall amino acid concentration levels specified in the present invention. Our invention is further premised on the discovery that the consumption of amino acids in medium formulated for perfusion (to stimulate production rather than proliferation) is reduced. Accordingly, such medium will support desired productivity with significantly lower concentrations of amino acids. Reductions in other feed elements such as glucose, vitamins, etc. is also feasible.

The perfusion process of the present invention is particularly well suited to the manufacture of the fusion protein known as etanercept (including biosimilar and bio better variants). Etanercept (Enbrel®) is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons (Physicians Desk Reference, 2002, Medical Economics Company Inc.) The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above. Etanercept is usually produced by recombinant DNA technology in a Chinese hamster ovary (CHO) mammalian cell expression system.

The perfusion process of the present invention is also well suited to the manufacture of the anti-TNF antibody known as adalimumab. Adalimumab (Humira®) is a recombinant human IgG1 monoclonal antibody specific for human TNF. Adalimumab is also known as D2E7. Adalimumab has two light chains, each with a molecular weight of approximately 24 kilodaltons (kDa) and two IgG1 heavy chains each with a molecular weight of approximately 49 kDa. Each light chain consists of 214 amino acid residues and each heavy chain consists of 451 amino acid residues. Thus, adalimumab consists of 1330 amino acids and has a total molecular weight of approximately 148 kDa. The term adalimumab is also intended to encompass so-called bio-similar or bio-better variants of the adalimumab protein used in commercially available Humira®.

The feed medium used in the present invention preferably comprises a base medium such as BalanCD®, and HyCell®, supplemented with dexamethasone. Cells producing a protein (e.g., etanercept or biosimilar or bio better variant thereof) are present in the perfusion vessel at a density of at least 10,000,000 cells/ml, and preferably at density of at least 5,000,000, and most preferably at least about 10,000,000 cells/ml. Prior to step (a), during a growth phase for the cells capable of expressing the desired protein (before substantial initiation of production), such cells capable of expressing the protein can be grown at a temperature selected from; (i) about 28° to about 37° C.; and (ii) preferably about 35° to about 36° C. During a subsequent production phase, involving perfusion processing, the etanercept production is carried out at a temperature selected from (i) greater than about 32°; (ii) greater than about 34°; (iii) greater than about 35° C.; (iv) the range of about 33° C. to about 36° C.; (v) the range of about 35° C. to about 36° C.; (vi) 32.5° C.; (vii) 33.5° C.; (viii) 34.5° C.; and (ix) 35.5° C. The method of the invention preferably comprises continuously or periodically, but preferably continuously, harvesting the etanercept during the production phase of the perfusion process. Moreover, the removal of spent medium and replacement with fresh culture medium occurs preferably continuously. Harvesting of the desired protein present in the continuously withdrawn culture medium is preferably carried out continuously.

The perfusion method of the present invention can be used for any therapeutic protein, including, e.g., fusion proteins and monoclonal antibodies. Examples of proteins suitable for production in the perfusion process of the invention include etanercept, adalimumab, trastuzumab, rituximab, bevacizumab, infliximab, eculizumab, and natalizumab, as well as biosimilar or bio better variants of such proteins. It should be understood however that the perfusion process of the present invention is not limited to any specific protein.

The volumetric productivity of the described process and the quality of the produced etanercept can be evaluated by using several methods well known to those skilled in the art. These methods include but are not limited to assays that quantify total and active protein (titers), qualify level of protein sialylation such as the isoelectric focusing (IEF) gels, hydrophobic Interaction chromatography and others.

The perfusion process of the present invention can produce correctly folded proteins in excellent yields, and preferably at production temperatures higher than those previously thought necessary or desirable in the art.

EXAMPLES

The following materials are used in the Examples.

TABLE 1

| Raw Material Description | Source | Vendor Catalog Number | Category | Useful Range | Use Notes |
| --- | --- | --- | --- | --- | --- |
| BalanCD ™ CHO Growth A | Irvine Scientific | 94120-10L | Base medium | n/a | base medium |
| HyClone ™ HyCell CHO | Thermo Scientific | SH30933 | Base medium | n/a | base medium |
| HyClone ™ SFM4CHO | Thermo Scientific | SH30518.04 | Base medium | n/a | used in seed train; |
| D-(+)-Galactose | SAFC | G5388 | Glycan feed | ≤10 | used at 10 mM final; to optimize product quality |

TABLE 1-continued

| Raw Material Description | Source | Vendor Catalog Number | Category | Useful Range | Use Notes |
|---|---|---|---|---|---|
| Dexamethasone | SAFC | D4902 | Glycan feed | ≤1 uM | used at 0.8-1.0 uM; to optimize product quality |
| ManNAc (N-acetylmannosamine) | SAFC | A8176 | Glycan feed | ≤20 | used at 10 mM final; to optimize product quality |
| BalanCD ™ CHO Feed 1 | Irvine Scientific | 94119-10L | Titer feed | 10% (v/v) | Boosts titer when added alone or with other titer feed |
| HyClone ™ Cell Boost 5 | Thermo Scientific | SH30865.04 | Titer feed | 10-20% (v/v) | Used in control experiments |
| Cottonseed Hydrolysate ("CSH") | FrieslandCampina Domo | CNE50M-UF | Titer feed | 15% (v/v) | increases specific productivity |
| EX-Cell CHOZN Platform Feed | SAFC | 24331C-10L | Titer feed | 10-20% (v/v) | complex feed for fed batch process |
| Growth Medium | SAFC | 87509CP | Base medium | n/a | Base medium for initial growth in production bioreactor |
| Production medium | SAFC | 87496CP | Complex medium | n/a | Complex medium for production phase in production bioreactor |
| Production medium | SAFC | 87612CP | Base medium | n/a | Base medium for production phase in production bioreactor |

Example 1

In this experiment we used feed media comprised of a 1:1 mixture of BalanCD™ CHO Growth A and HyClone™ HyCell media supplemented with EX-CELL CHOZN and Feed 1 feeds, cotton seed hydrolysate, galactose, L-glutamine, and glucose. Some conditions involved additional supplementation with vitamins, amino acids, and higher concentrations of CHOZN and Feed 1, making the medium significantly richer (See SF5, SF6 and SF7, below). Prior to addition of the feed media, the seed density was 40 million cells per milliliter of culture. Perfusion processing was simulated in that culture received complete exchange of medium 24 hours after seeding and the culture was then continued for 96 hours (with no further feeding or media exchange). Culture performance was monitored with respect to viable cell density, viability, metabolic profile (ammonia and lactate production, L-glutamine and glucose consumption, pH levels, glutamate production), and productivity. As shown in the data presented below, cultures with greater vitamin and amino acid supplementation (see SF5 and SF6, below) produced very high levels of ammonia (>40 mM) resulting in premature decline of viability. We did not observe any other metabolic changes when compared to data obtained for the surviving cells other than the exceptionally high ammonia levels. The titers obtained on the higher-nutrient nutrient media were also negatively affected even during the time when the viability was comparable between all cultures. The lower nutrient cultures without the extra vitamins and amino acids (SF3 and SF4) remained at high viability, had good productivity, and yielded material of good product quality (see Data section below).

This Example 1, using a single feed replacement at 24 hr, followed by a 96 hr production phase (without further media exchange during the 96 hour period) demonstrates that a medium intended for use in perfusion (in which media is continuously or periodically exchanged) will necessarily require reduced levels of nutrients, at levels lower than that used for the feeds in SF3 and SF4. Accordingly, as provided in Examples 2 and 3 below, feed media used in a perfusion process should employ a total amino acid content of less than 70 mM and preferably a total amino acid content in the range of about 15 to about 30 mM, yet still result in excellent cell density, cell viability and production titer. Total amino acid content as used herein should be understand to mean the total, steady state, amino acid concentration based on the volume of the perfusion reaction vessel.

Results of Example 1

Table 1, below, summarizes the feed media used in five experiments (SF3 through SF7) in which, as described above, media is exchanged, after seeding, at 24 hours, and the process is then allowed to continue (without any further media exchange) for an additional 96 hours. This experiment compared lower nutrient feeds (runs SF3, SF4) with higher nutrient feeds (runs SF5, SF6, SF6 and SF7). The feeds shown in the Table were used to supplement a base medium consisting of BalanCD and Hycell (as identified in the materials listing, above). Vitamins (Invitrogen, cat#11120-052) and amino acids (Invitrogen, cat#11130-036) were added as 1× concentration from 100× stock.

TABLE 2

PERFUSION FEEDS

| Feeds | SF3 Lower Nutrient Feed | SF4 Lower Nutrient Feed | SF5 Higher Nutrient Feed | SF6 Higher Nutrient Feed | SF7 Higher Nutrient Feed |
|---|---|---|---|---|---|
| CHOZN | 10% | 10% | 10% | 10% | 20% |
| CSH |  | 7.5% | 7.5% | 7.5% |  |
| Feed 1 | 10% | 10% | 10% | 10% | 20% |
| L-Gln | 8 mM | 8 mM | 8 mM | 8 mM | 8 mM |
| Vitamins |  |  | 1x | 1x |  |
| AA |  |  |  | 1x |  |
| Gal | 10 mM | 10 mM | 10 mM | 10 mM | 10 mM |

FIG. 1 sets forth data on viable cell density (VCD) of cultures containing the lower concentrations feeds (SF3 and SF4) in accordance with the present invention. Note that very high culture densities were obtained. Relatively leaner medium (10% CHOZN+7.5% cotton seed hydrolysate (CSH) and 10% Feed 1, and with no additional supplementation with vitamins or amino acids) (see SF3 and SF4) provided sufficient nutritional support for cells to sustain high viability for at least 96 hours.

Figure 2:
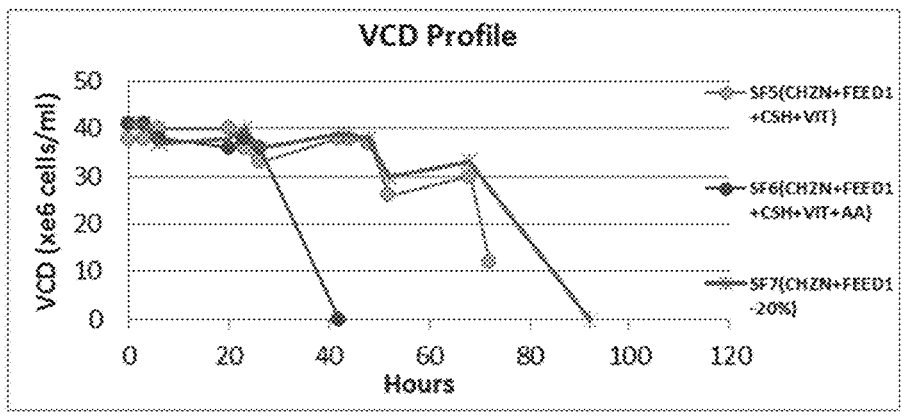
FIG. 2 is a chart of VCD of cultures containing more highly enriched nutrient media.

FIG. 2 demonstrates (in the case of Feeds SF5, SF6 and SF7) that the more highly enriched nutrient media (resulting from supplementation with vitamins and amino acids or complex feeds) resulted in reduced culture longevity. In particular, we discovered that addition of amino acids at concentrations that appear to exceed the metabolic requirements of the culture results in a rapid decline of viability. It was further noted that all cultures with shorter longevity (e.g., SF6 and SF7) produced high levels of ammonia (see FIG. 3).

Figure 3:
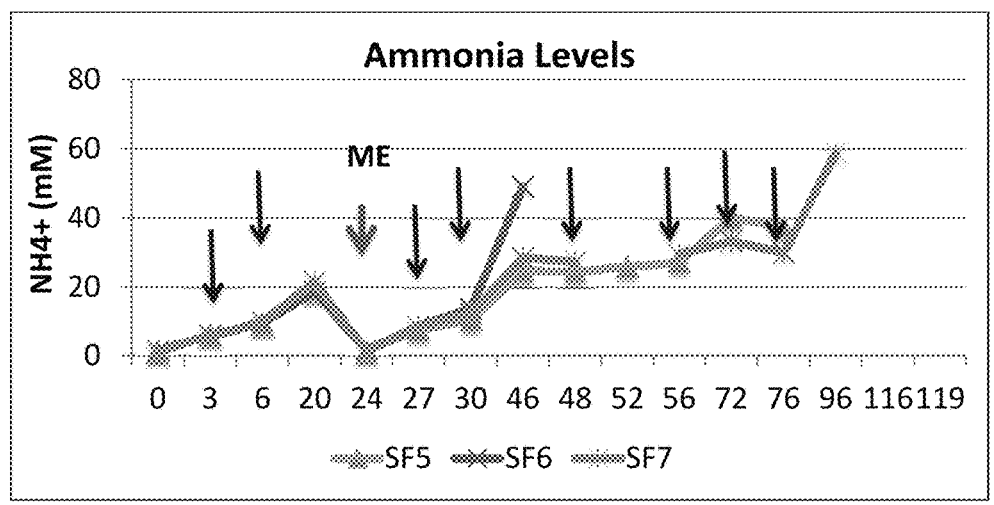
FIG. 3 is a chart of ammonia levels in the cultures containing more highly enriched nutrient media.

FIG. 3 shows that cultures (see SF6 and SF7 in Table 2 above) using the higher nutrient feed media display unacceptably high production of ammonia which we postulate may cause or contribute to premature decline of viability.

Figure 4:
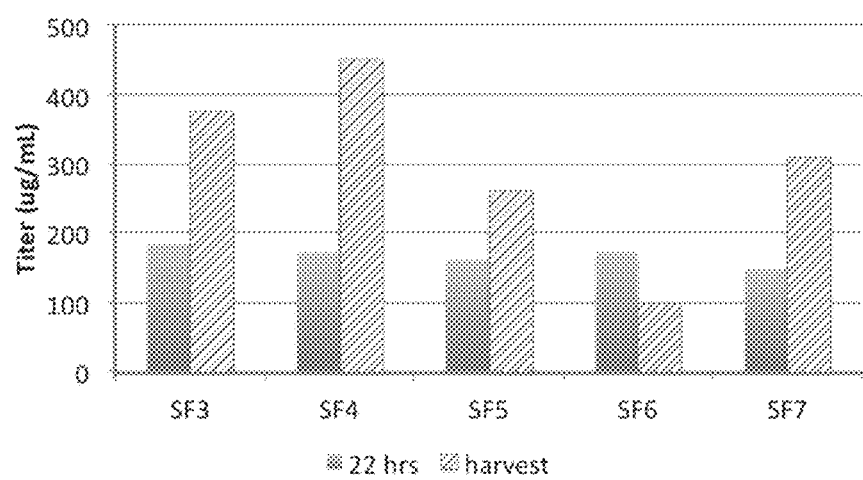
FIG. 4 is a bar chart of protein production in the reduced nutrient media and the more highly enriched nutrient media.

FIG. 4 shows that protein production in the higher nutrient medium (e.g., SF5, SF6 and SF7) is negatively affected as shown by reduced titers. Compare the production from cultures using the reduced nutrient feeds of SF3 and SF4 according to the invention with the production achieved from cultures using the more highly enriched feeds of SF5, SF6 and SF7.

Example 2

Based on the data obtained in Example 1, and in accordance with our invention, we find that a medium with reduced nutrients, such as that employed in runs SF3 and SF4 in Example 1 above, can be modified to further substantially reduce total amino acid concentration when employed in a perfusion process undergoing continuous or periodic media replacement. In particular, in such a perfusion process, a total concentration of amino acids less than 70 mM, and preferably in the range of about 15 mM to about 65 mM, and most preferably in the range of about 20 mM to about 30 mM will support the metabolic needs of the cell culture in a perfusion process for manufacturing therapeutic proteins such as, for example, a TNFR-Fc fusion protein, or a anti-TNF monoclonal antibody. Accordingly, in a perfusion process involving periodic media replacements, a perfusion process according to the invention is employed in which feed media, having total amino acid concentration of less than 70 mM and preferably in the range of about 15 to about 65 mM, and most preferably about 20 to about 30 mM is replaced every 24 hours with fresh medium. Such a process which simulates perfusion is equivalent to a perfusion rate of 1 bioreactor volume per day. Cells are inoculated at a density of preferably 50 million cells per milliliter, and medium is exchanged every 24 hours for a total of 3 exchanges. The culture is terminated on day 4 (total time 96 hours). Viable cell density and viability is noted daily. Titer and isoform profile reflecting product quality are determined for each harvest sample using appropriate assays known in the art. Cells may require approximately 3 days (72 h) to gradually switch the metabolism to production mode as reflected by improved titer and product quality (96 h samples). The process results in excellent cell density and cell viability as well as excellent titer, notwithstanding the use of feed media containing substantially lower total amino acid concentrations as compared to media typically employed in fed batch processes, such as recommended in U.S. Pat. No. 7,300,773 in which the total cumulative amino acid concentration is required to exceed 70 mM.

Example 3

Perfusion with Continuous Media Replacement

Example 2 is repeated, except that a continuous perfusion process is employed in which fresh media is continuously introduced to the reactor, and spent media is continuously removed in a manner well known in the art, whereby, in accordance with the present invention, the steady state total amino acid concentration of the feed media in the reactor is less than 70 mM, and preferably in the range of 15 to about 65 mM, and most preferably in the range of about 20 to about 55 mM. The continuous perfusion process results in excellent cell density, cell viability and titer. In addition to the requirements for total amino acid concentration, the feed medium is preferably formulated such that at the steady state media concentration in the perfusion reactor one or more of the following criteria are met: (i) a steady state total amino acid amount per unit volume less than about 70 mM; (ii) a steady state glutamine to cumulative asparagine ratio of greater than about 2; (iii) a steady state glutamine to total amino acid ratio of greater than about 0.2; (iv) a steady state molar inorganic ion to total amino acid ration greater than 1; and (v) a steady state combined amount of glutamine and asparagine per unit volume of less than 16 mM. The term steady state is intended to denote that the concentration and ratio of feed components, as expressed above, remain essentially constant at the stated levels in the perfusion reaction vessel.

Example 4

Figure 5:
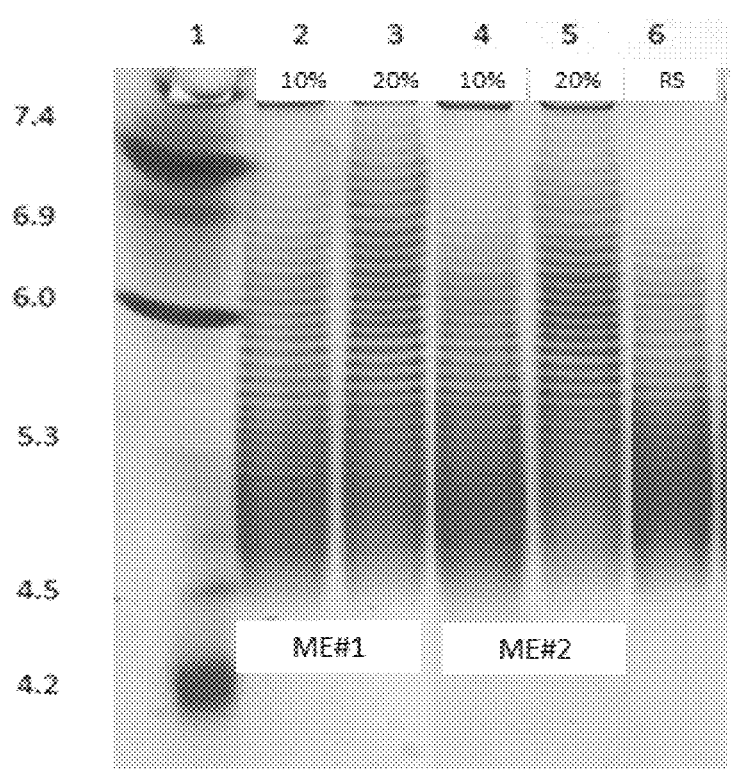
FIG. 5 is a picture of an isoelectric focusing (IEF) gel that contains distribution of charged species of SFM4CHO basal medium supplemented with two different concentrations of Cell Boost 5 feed, as well as that of commercial etanercept (Enbrel®).

We evaluated various media compositions allowing for robust culture performance under perfusion conditions with respect to growth, productivity, and product quality. In one of our experiments achieving cell density of 10 million cells per milliliter we tested SFM4CHO basal medium supplemented with two different concentrations of Cell Boost 5 feed and found that leaner (10% feed), resulting in a total amino acid concentration of approximately 50 mM, resulted in better product quality than a culture that was supplemented with 20% feed resulting in a total amino acid concentration of approximately 100 mM. The difference in quality is demonstrated by the data shown in FIG. 5). Lanes 2 and 4 show a distribution of charged species very similar to that for commercial etanercept (Enbrel®) (lane 6), with a preponderance of acidic bands migrating further into the gel. In contrast, samples from the richer feeds (lanes 3 and 5) show less of the acidic, rapidly-migrating species and are less similar to Enbrel®.

A subsequent experiment tested higher culture densities (25 million cells per ml) using exactly the same feed conditions. We found that the medium formulation with the lower content of Cell Boost 5 feed was unable to sustain culture viability, ultimately resulting in decline of product quality. However, we also found that while the feed medium containing the higher total amino acid concentration (approx. 100 mM) did support a high viability, the product quality was not comparable to that observed at the lower cell density. This outcome necessitated further investigations to find other media and feeds that could provide good product quality while supporting cell densities of 25-50 million cells per ml. We therefore investigated several based media and media combinations in batch mode in order to identify media compositions that were able to support the highest longevity of cultures seeded at 30 to 50 million cells per mL of culture. This investigation included the experiment and finding set forth in Example 1 above.

Example 5

Media Requirements in the Perfusion Production of a TNFR-Fc Fusion Protein

Figure 6:
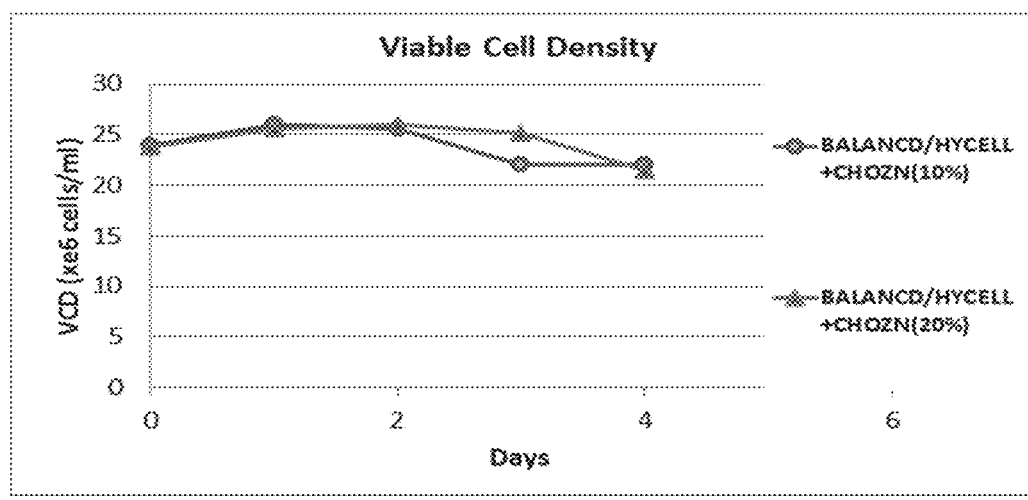
FIG. 6 is a chart of VCD of cultures containing 10% and 20% CHOZN feed.
Figure 7:
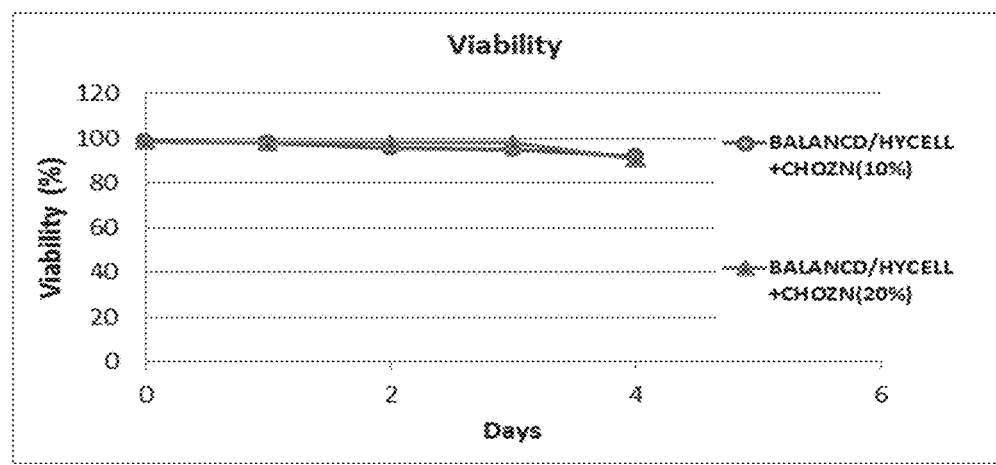
FIG. 7 is also a chart of VCD of cultures containing 10% and 20% CHOZN feed.

We conducted a variety of medium exchange experiments simulating perfusion using high density cultures ($25 \times 10^6$ cells/ml) in the production of a TNFR-Fc fusion protein under development as a biosimilar to etanercept. In these experiments we consistently found that high viability can be achieved with feeds that provide reduced concentrations of nutrients. Our findings are exemplified by an experiment in which two high density cultures were established, each containing 25 million cells per milliliter of culture, both cultures utilized the same base medium (BalanCD/Hycell, 1:1) and additional supplementation with 10 mM galactose and 10 mM ManNAc. The difference between both cultures was in the level of supplementation with CHOZN feed (10% versus 20%) and cottonseed hydrolysate (7.5% versus 15%). Both feeds provided additional amino acid supplies to the cultures. Viability of the culture with the lower concentration of feeds matched that of the culture that received the richer medium. This result indicated that reduction of feed concentration from 20% (98 mM total amino acid content) to 10% (78 mM total amino acid content) did not limit the nutritional requirements of that culture and clearly indicated that the total amino acid concentration could be reduced further to the levels that we have now prescribed in the present invention. Data is shown in FIG. 6 and FIG. 7.

Spent media analysis with respect to amino acid content showed that culture with lower feed content, even after 48 hours of cultivation, did not deplete in a significant way any of the amino acid provided. This demonstrates that amino acid content is higher than the culture's nutritional requirements and in accordance with the present invention can be further reduced below the level of 78 mM. Accordingly, we find that cells perfused with medium at a constant rate will need much lower levels of amino acids, and that the rate of perfusion equal to 1 bioreactor volume per day should require a steady state total amino acid concentration in the range of about 20-50 mM.

One of the primary requirements in product development projects is the high titer expression of product with the desired quality. Most proteins require proper posttranslational modification for their therapeutic activities. For example, the TNFR-FC fusion protein produced in this Example requires a significant degree of sialylation resulting in a specific distribution of isoforms based on a molecular charge profile. Isoelectric focusing analysis shown by IEF gel (FIG. 8) demonstrates that reduction of feed content did not result in alteration of the product isoform distribution as compared to commercial reference standard and samples obtained from cultures fed with 20% feed.

Figure 8:
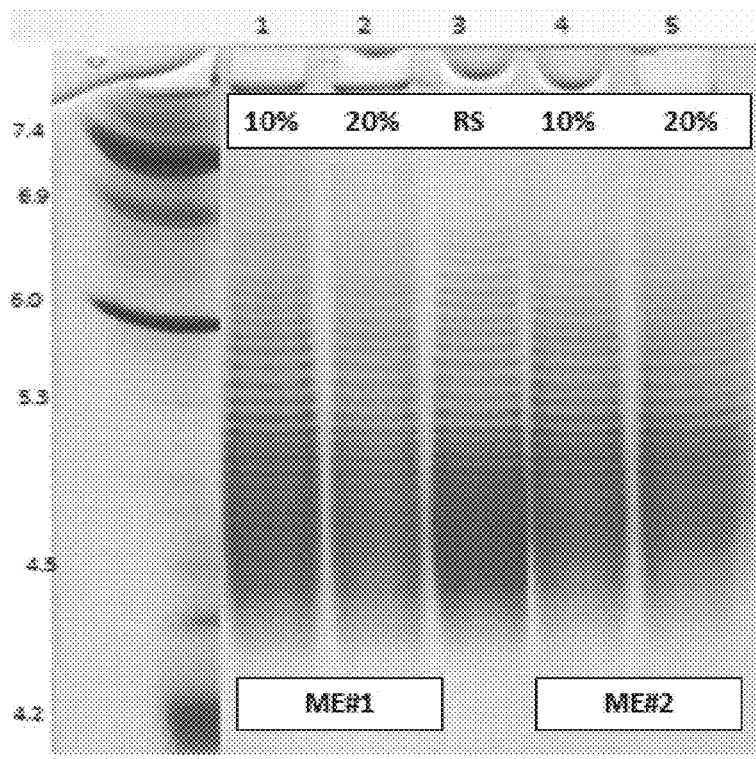
FIG. 8 is a picture of an IEF gel that contains isoform distribution in product isolated from cultures containing 10% and 20% feed cultures; as well as that of reference standard.

In FIG. 8 isoelectric focusing (IEF) gel shows comparable isoform distribution in product isolated from cultures containing lower (10%) feed concentration (shown in wells 1 and 4, first and second medium exchange, ME), as compared to that isolated from amino acid rich (20%) feed cultures (shown in wells 2 and 5, first and second medium exchange, ME). Profile of reference standard is shown in well 3.

Figure 9:
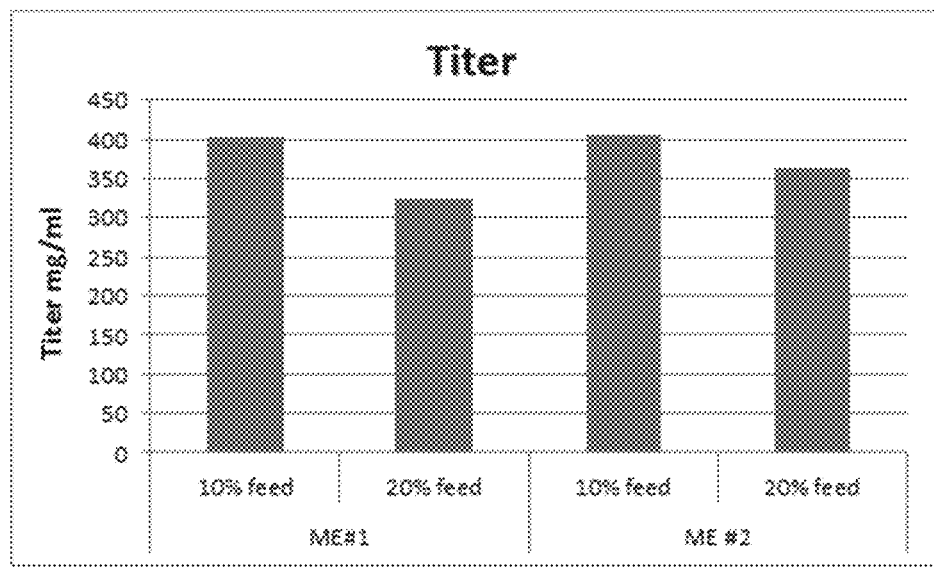
FIG. 9 is a bar chart of protein production in the cultures containing leaner (10%) and richer (20%) feed concentration.

As seen in FIG. 9, titers obtained for cultures fed with leaner (10% feed) and richer (20%) show that higher concentration of feeds can result in lower culture productivity. By providing cells with the nutrient requirements for perfusion specified in the present invention, and thus avoiding unnecessarily rich medium, one can achieve a culture metabolic state in perfusion processing that results in better productivity and product quality compared to media requirements heretofore recommended in the art (see, e.g., U.S. Pat. No. 7,300,773).

Example 6

For production of a TNFR-Fc fusion protein under development as a biosimilar of etanercept, the seed train is expanded in large-volume shake flasks at 37° C. in SFM4CHO. The production bioreactor is inoculated at seeding densities of from 1 to $5 \times 10^6$ cells/mL in medium where the total amino acid concentration is varied in nine separate repetitions of this experiment from about 15 to about 70 mM (see Table 3, below). In each of the runs, temperature during a production phase (with continuous perfusion) is from 33.5° C. to 35° C. An ATF™cell retention device (Refine Technology) is used to recirculate medium (containing waste products and desired product) past a hollow fiber filter, with recirculation rates from 0.05 to 2.0 working culture volumes per minute. The culture is first expanded in a growth phase for 0 to 2 days, and then perfusion is initiated at rates from 0.2 to 2 culture volumes per day to facilitate a production phase. New medium is added, as spent medium (containing the product) is harvested through a 0.2 um pore size hollow fiber filter. Harvested fluid is chilled to 2-8° C., purified by capture on protein A resin. Aliquots are analyzed for titer and for product quality attributes such as N-glycan distribution and HIC analysis (to evaluate the relative amounts of properly folded etanercept, versus improperly folded/aggregated (inactive) material). The total amino acid concentrations investigated in these runs is shown below:

TABLE 3

Total (Steady State) Amino Acid Concentration (approx.)

| RUN # 1 | 15 to 20 mM |
|---|---|
| RUN # 2 | 20-25 mM |
| RUN # 3 | 25-30 mM |
| RUN # 4 | 30-35 mM |
| RUN # 5 | 35-40 mM |
| RUN # 6 | 45-50 mM |
| RUN # 7 | 55-60 mM |
| RUN # 8 | 60-65 mM |
| RUN # 9 | 65-70 mM |

Analysis of the viable cell density, viability, product quality and titer for each of runs 1 through 9 demonstrates excellent results with respect to these characteristics at the lower end of the total amino acid concentration range of 15 to 70 mM, preferably in the range of about 15 to about 30 mM, with increasing deterioration in these characteristics as one progresses to the higher end of the range.

Example 7

For production of a TNFR-Fc fusion protein under development as a biosimilar of etanercept, the seed train was expanded in large-volume shake flasks at 37° C. in SFM4CHO. The production bioreactor was inoculated at seeding densities of from 0.3 to 0.75×10$^6$ cells/mL in a series of perfusion bioreactors in medium where the total amino acid concentration was about 20 to about 56 mM. In each of the runs, temperature during a production phase (with continuous perfusion) was 35 to 37° C. An ATF™ cell retention device (Refine Technology) was used to recirculate medium (containing waste products and desired product) past a hollow fiber filter, with recirculation rates from 0.5 to 2.0 working culture volumes per day. The culture was first expanded in a growth phase for up to 8 days, with perfusion at a cell-specific perfusion rate of 0.05 to 0.1 nL per cell per day. The temperature was reduced to, for example, 33.5° C. to facilitate a production phase. New medium was added, as spent medium (containing the product) was harvested through a 0.2 um pore size hollow fiber filter. Harvested fluid was chilled to 2-8° C., in preparation for capture on protein A resin. Aliquots were analyzed for titer and for product quality attributes such as N-glycan distribution and HIC analysis (to evaluate the relative amounts of properly folded etanercept, versus improperly folded/aggregated (inactive) material).

Figure 10:
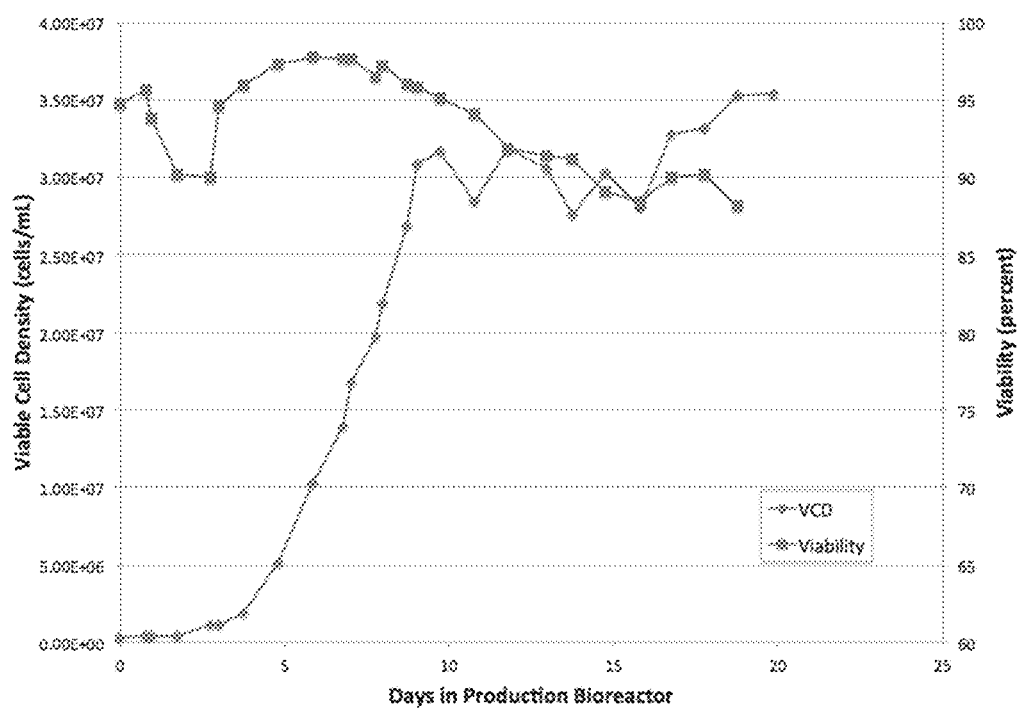
FIG. 10 is a chart of VCD and viability of culture grown as described in Example 7.

Analysis of the viable cell density, viability, product quality and titer for each run demonstrated excellent results with respect to these characteristics at the lower end of the total amino acid concentration range of 20 to 56 mM, preferably in the range of about 15 to about 30 mM. As shown in FIG. 10, a culture grown as described here achieved about 30 million cells/mL during a nine-day growth phase and maintained that cell concentration at high viability during a production phase that extended for an additional 11 to 12 days.

What is claimed is:

1. A method for manufacturing a protein comprising the step of producing the protein via perfusion in the presence of a feed medium comprising a total amino acid concentration of less than 70 mM, wherein a protein titer of at least 300 μg/mL is achieved in the step of producing the protein, and wherein the protein is a TNFR (tumor necrosis factor receptor)-Fc fusion protein or an anti-TNF antibody.

2. The method of claim 1 wherein the feed medium comprises a total amino acid concentration in a range selected from the group consisting of: 15 to 20 mM; 20 to 25 mM; 25 to 30 mM; 30 to 35 mM; 35 to 40 mM; 40 to 45 mM; 45 to 50 mM; 50 to 55 mM; 55 to 60 mM; 60 to 65 mM; and between 65 and 70mM.

3. The method of claim 1 wherein the protein is selected from the group consisting of etanercept, adalimumab, infliximab, and a biosimilar thereof.

4. The method of claim 1 wherein the feed medium comprises one or more of the following: a base medium, cottonseed hydrolysate, dexamethasone, ManNAc (N-acetylmannosamine), and/or D-(+)-Galactose.

5. The method of claim 1 further comprising prior to the protein production step, preparing a mixture comprising cells capable of expressing a desired therapeutic protein, and a culture medium suitable for conducting such expression; and wherein the protein production step comprises (a) in a suitable vessel containing the mixture, causing the cells to produce the protein, and (b) periodically or continuously removing spent culture medium from, and adding fresh culture medium to, the vessel.

6. The method of claim 5 where the cells are CHO (Chinese hamster ovary) cells.

7. The method of claim 5 wherein, prior to the protein production step, the cells capable of expressing the protein are grown in a growth phase at a temperature selected from (i) 28° to 37° C.; and (ii) 35° to 36° C.

8. The method of claim 7 wherein the protein production step is carried out at a temperature selected from (i) greater than 32° C.; (ii) greater than 34° C.; (iii) greater than 35° C.; (iv) the range of 33° C. to 36° C.; (v) the range of 35° C. to 36° C.; (vi) 32.5° C.; (vii) 33.5° C.; (viii) 34.5° C.; and (ix) 35.5° C.

9. The method of claim 8 wherein the protein being produced is selected from the group consisting of etanercept, adalimumab, infliximab, and a biosimilar thereof.

10. A perfusion method for producing a therapeutic protein comprising the steps of (a) preparing a mixture comprising CHO cells capable of expressing the protein, and a culture medium suitable for conducting such expression; (b) in a suitable vessel containing the mixture, causing the cells to produce the protein; and (c) periodically or continuously removing spent culture medium from, and adding fresh culture medium to, the vessel, wherein the culture medium comprises (i) a total amino acid concentration of 15 to 65 mM; and (ii) at least one selected from the group consisting of: a complex chemically-defined feed, dexamethasone, ManNAc (N-acetylmannosamine), cottonseed hydrolysate and D-(+)-galactose; wherein a protein titer of at least 300 μmL is achieved in the step of producing the protein, and wherein the therapeutic protein is a TNFR (tumor necrosis factor receptor)-Fc fusion protein or an anti-TNF antibody.

11. The method of claim 10 wherein the therapeutic protein is selected from the group consisting of etanercept, adalimumab, infliximab, and a biosimilar thereof.

12. The method of claim 11 wherein the therapeutic protein is etanercept, or a biosimilar thereof.

13. The perfusion method of claim 12 wherein, prior to step (a), the cells capable of expressing etanercept or a biosimilar thereof are grown in a growth phase at a temperature selected from; (i) 28° C. to 37° C.; and (ii) 35° to 36° C.

14. The perfusion method of claim 13 wherein, during production of the etanercept or biosimilar thereof occurring in steps (b) and (c) the vessel is maintained at a temperature selected from (i) greater than 32° C.; (ii) greater than 34° C.; (iii) greater than 35° C.; (iv) the range of 33° C. to 36° C.; (v) the range of 35° C. to 36° C.; (vi) 32.5° C.; (vii) 33.5° C.; (viii) 34.5° C.; and (ix) 35.5° C.

* * * * *